United States Patent
Kramer et al.

(10) Patent No.: US 9,927,402 B2
(45) Date of Patent: Mar. 27, 2018

(54) METHOD FOR MEASURING A FLUID DENSITY OR A FLUID VISCOSITY

(71) Applicant: ABB Schweiz AG, Baden (CH)

(72) Inventors: Axel Kramer, Wettingen (CH); Hubert Brandle, Oberengstringen (CH); Thomas Alfred Paul, Waedenswil (CH)

(73) Assignee: ABB Schweiz AG, Baden (CH)

( * ) Notice: Subject to any disclaimer, the term of this patent is extended or adjusted under 35 U.S.C. 154(b) by 634 days.

(21) Appl. No.: 14/444,561

(22) Filed: Jul. 28, 2014

(65) Prior Publication Data

US 2014/0331766 A1    Nov. 13, 2014

Related U.S. Application Data

(63) Continuation of application No. PCT/EP2012/051322, filed on Jan. 27, 2012.

(51) Int. Cl.
*G01N 9/02* (2006.01)
*G01N 29/036* (2006.01)
(Continued)

(52) U.S. Cl.
CPC ........... *G01N 29/036* (2013.01); *G01N 9/002* (2013.01); *G01N 9/34* (2013.01); *G01N 11/16* (2013.01);
(Continued)

(58) Field of Classification Search
None
See application file for complete search history.

(56) References Cited

U.S. PATENT DOCUMENTS

| 4,734,609 | A | * | 3/1988 | Jasmine | G01L 9/0022 |
| | | | | | 310/311 |
| 4,862,384 | A | * | 8/1989 | Bujard | G01N 11/00 |
| | | | | | 702/54 |
| 2006/0031030 | A1 | * | 2/2006 | Bennett | G01F 23/2967 |
| | | | | | 702/50 |

FOREIGN PATENT DOCUMENTS

| EP | 0582045 A1 | 2/1994 |
| WO | 2010043268 A1 | 4/2010 |

OTHER PUBLICATIONS

Zeisel, et al., "A Precise and Robust Quartz Sensor Based on Tuning Fork Technology for (SF6)-gas Density Control", Sensors and Actuators 80 (2000) pp. 233-236.
(Continued)

*Primary Examiner* — Paul West
*Assistant Examiner* — Mark A Shabman
(74) *Attorney, Agent, or Firm* — Whitmyer IP Group LLC

(57) ABSTRACT

A method and device for estimating a density value $\rho_m$ indicative of a true density $\rho$ or for estimating a viscosity value $\eta_m$ indicative of a true viscosity $\eta$ of a fluid is disclosed. For this, a first resonance frequency $f_R$ of a first mechanical oscillator in a reference volume and a second resonance frequency $f_F$ of a second mechanical oscillator in contact with the fluid are measured. The estimated value $\rho_m$ or $\eta_m$ is then derived using these resonance frequencies $f_R$ and $f_F$. During this derivation, at least one fluid-temperature- or fluid-pressure-dependent parameter of the fluid is used. Additionally or alternatively, the first (i.e. reference) mechanical oscillator is arranged in contact with a reference fluid. Thus, fundamental errors in the derivation of the estimated value $\rho_m$ or $\eta_m$ are reduced and the estimated value becomes more reliable.

15 Claims, 4 Drawing Sheets

(51) Int. Cl.
G01N 29/02 (2006.01)
G01N 29/44 (2006.01)
G01N 9/34 (2006.01)
G01N 11/16 (2006.01)
G01N 9/00 (2006.01)

(52) U.S. Cl.
CPC ....... G01N 29/022 (2013.01); G01N 29/4472 (2013.01); *G01N 2009/006* (2013.01); *G01N 2291/02818* (2013.01); *G01N 2291/0427* (2013.01)

(56) References Cited

OTHER PUBLICATIONS

International Preliminary Report on Patentability Application No. PCT/EP2012/051322 Completed: Jul. 10, 2014 24 pages.
International Search Report and Written Opinion of the International Searching Authority Application No. PCT/EP2012/051322 Completed: Oct. 12, 2012; dated Oct. 22, 2012 13 pages.
Seil, et al., "Real-Time Monitoring of a High Pressure Reactor Using a Gas Density Sensor", Sensors and Actuators A 162 (2010) pp. 215-219.

* cited by examiner

METHOD FOR MEASURING A FLUID DENSITY OR A FLUID VISCOSITY

FIELD OF THE INVENTION

The present invention relates to a method for deriving an estimated value which is indicative of a fluid density $\rho$ or of a fluid viscosity $\eta$. Furthermore, the present invention relates to devices implementing such a method.

BACKGROUND OF THE INVENTION

Mechanical resonators can be used to measure the density or viscosity of fluids.

One possible application of such measurement systems is the monitoring of SF6 insulation gas in gas insulated electrical apparatuses such as medium or high voltage switchgear. However, because SF6 is a potent green house gas, governmental regulations are becoming stricter. This results in tighter licensing and operation requirements for plant owners. As a result, more precise monitoring technology is needed to be able to detect, e.g., SF6 gas leakage more precisely.

In other possible applications, the determination of concentrations of individual components in gas mixtures is the key goal. This problem can be addressed by measuring the total gas mixture pressure p, the total gas mixture temperature T, and the total gas mixture density $\rho$ and deriving the component concentrations from these measurement parameters. If the concentration of one or more components in the gas mixture is low, however, or if a component's concentration has to be measured with higher precision, a more accurate density measurement system is required.

Other possible applications for density measurement systems are, e.g., the monitoring of chemical and pharmaceutical processes, energy content determination in gas metering, or higher precision altitude metering, e.g., for aeronautics.

EP 0 582 045 B1 and WO 2010043268 A1 describe methods and devices for measuring gas densities. These implementations are based on two resonantly vibrating quartz tuning forks which are low-cost parts in microelectronics. One of these quartz tuning forks is arranged in an evacuated reference chamber while the other one is in contact with the to-be-measured gas or gas mixture. Due to the interaction between the gas or gas mixture and the respective tuning fork, the resonance frequency of this tuning fork is shifted. The amount of this frequency shift is then used to derive a density readout value for the gas or gas mixture.

The disclosed methods and devices have the disadvantage, however, that gas density readings obtained from them are susceptible to frequently encountered fundamental errors. Thus, the density readout values are not as accurate as desired.

SUMMARY OF THE INVENTION

Hence it is a general objective of the present invention to provide an improved method for deriving an estimated value which is indicative of a fluid density or a fluid viscosity. It is a further objective of the invention to provide a sensor that implements such a method. Another objective of the invention is to provide an electrical apparatus comprising such a sensor. Yet another objective of the invention is to provide a computer program element that implements such a method for deriving such an estimated value.

These objectives are achieved by the method and devices of the independent claims.

Accordingly, a method for deriving at least one estimated or determined value $\rho_m$, which is indicative of a density $\rho$ of a fluid, or for deriving at least one estimated or determined value $\eta_m$, which is indicative of a viscosity $\eta$ of a fluid, comprises the step of measuring a first resonance frequency $f_R$ of a resonant vibration of a first mechanical oscillator and the step of
measuring a second resonance frequency $f_F$ of a resonant vibration of a second mechanical oscillator.

The measurement of additional resonance frequencies and/or other parameters is possible. The mentioned steps can be carried out one after another with no specific order, or they can be carried out concurrently. The first mechanical oscillator is arranged in a reference volume and it is secluded from the fluid, whose density or viscosity is to be quantified. The term "secluded from the fluid" in this respect means that the first mechanical oscillator is not in contact with the to-be-measured fluid. The second mechanical oscillator is arranged in a measurement volume, which comprises the to-be-measured fluid, and the fluid is in direct or indirect (e.g., through a semi-permeable membrane) contact with the second mechanical oscillator. The fluid in the measurement volume has a fluid temperature $T_F$ and a fluid pressure $p_F$. The second mechanical oscillator and the fluid are advantageously in a thermal equilibrium, i.e., the mechanical oscillator has a temperature that is equal to the fluid temperature $T_F$. More advantageously, the first mechanical oscillator is in a thermal equilibrium with the second mechanical oscillator, i.e., both oscillators have the same temperature.

The method further comprises the step of
deriving the estimated or determined value $\rho_m$ or $\eta_m$ (e.g. the measurement value for $\rho$ or $\eta$ of the fluid) using the first resonance frequency $f_R$ and the second resonance frequency $f_F$ and/or any derived quantity from these resonance frequency values, e.g. the absolute value of their difference. For said derivation of said estimated value $\rho_m$ or $\eta_m$, the fluid temperature $T_F$ and/or the fluid pressure $p_F$ and/or at least one parameter which is dependent on the fluid temperature $T_F$ and/or on the fluid pressure $p_F$ is or are used. Thus, fundamental errors in deriving the estimated value $\rho_m$ or $\eta_m$ owing to fluid-temperature- and/or fluid-pressure-dependent effects (e.g. viscosities) can be avoided or reduced during the derivation of $\rho_m$ or $\eta_m$.

Alternatively or additionally to using the fluid-temperature $T_F$ and/or the fluid-pressure $p_F$ and/or at least one $T_F$- and/or $p_F$-dependent parameter for the derivation of $\rho_m$ or $\eta_m$, the first mechanical oscillator (i.e. the mechanical oscillator that is not in contact with the to-be-measured fluid) is in contact with a reference fluid. In other words, the first mechanical oscillator is not arranged in an evacuated reference chamber, but it is in contact with a reference fluid. This reference fluid can be the same or a different compound or mixture as the to-be-measured fluid. The reference fluid has a reference fluid temperature $T_R$ and a reference fluid pressure $p_R$. By establishing such a contact between the first mechanical oscillator and the reference fluid, fundamental errors during the derivation of $\rho_m$ or $\eta_m$ can also be intrinsically avoided or reduced. This is because the first mechanical oscillator and thus the first resonance frequency $f_R$ is subject to an interaction with the reference fluid.

Both error reduction approaches—using the fluid temperature $T_F$ and/or the fluid pressure $p_F$ and/or at least one parameter which is dependent on the fluid temperature $T_F$ and/or on the fluid pressure $p_F$ for the derivation of $\rho_m$ or $\eta_m$ on the one hand and establishing a contact between the first mechanical oscillator and a reference fluid on the other hand—are based on the same principle idea that fundamental errors in the derivation of $\rho_m$ or $\eta_m$ can be avoided or reduced by taking into account a temperature and/or a pressure, either computationally in the derivation step of $\rho_m$ or $\eta_m$ itself or intrinsically via the contact between the first mechanical oscillator and the reference fluid.

A combination of both error reduction approaches is also possible.

When the first mechanical oscillator is in contact with a reference fluid, this reference fluid is advantageously comprised in said reference volume and its temperature $T_R$ (in Kelvin) is equal to or differs less than ±5%, preferably less than ±2%, more preferably less than 1% from said fluid temperature $T_F$. This has the advantage that the fluid and the reference fluid have the same temperature or at least similar temperatures $T_R$ and $T_F$ which makes it easier to avoid or reduce fundamental errors during the derivation of the estimated value $\rho_m$ or $\eta_m$. More advantageously, the two mechanical oscillators and the fluid and the reference fluid are in a thermal equilibrium.

More advantageously, when the first mechanical oscillator is in contact with the reference fluid, the reference fluid pressure $p_R$ is set (e.g. at filling time of the reference volume) to be at most 0.1 mbar, preferably at most $10^{-2}$ mbar, more preferably at most $10^{-4}$ mbar as measured over a reference fluid temperature range of $T_R>200$ K and $T_R<400$ K. The interaction between the first mechanical oscillator and the reference fluid becomes weaker and weaker with decreasing reference fluid pressures $p_R$ below 0.1 mbar until "no reference fluid" is effectively present any more. Thus, e.g. a low-cost commercially available encapsulated and evacuated off-the-shelf quartz tuning fork can be used as first mechanical oscillator, which reduces costs. Fundamental errors in the derivation of $\rho_m$ or $\eta_m$ can then be avoided or reduced by using the fluid temperature $T_F$ and/or the fluid pressure $p_F$ and/or at least one parameter which is dependent on the fluid temperature $T_F$ and/or on the fluid pressure $p_F$ for the derivation of $\rho_m$ or $\eta_m$.

In a different advantageous embodiment, when the first mechanical oscillator is in contact with the reference fluid, the reference fluid pressure $p_R$ is set (e.g. at filling time of the reference volume) to be at least 1 mbar, preferably at least 10 mbar, more preferably at least 100 mbar, even more preferably at least 1 bar as measured over a reference fluid temperature range of $T_R>200$ K and $T_R<400$ K. Thus, a higher reference fluid pressure $p_R$ can be used which further reduces fundamental errors (owing, e.g., to a pressure-dependence of the fluid viscosity) during the derivation of $\rho_m$ or $\eta_m$.

In another advantageous embodiment, when the first mechanical oscillator is in contact with the reference fluid, the fluid pressure $p_F$ and the reference fluid pressure $p_R$ are equal or differ less than by a factor of 10, preferably less than by a factor of 5, more preferably less than by a factor of 2. Thus, fundamental errors during the derivation of $\rho_m$ or $\eta_m$ are reduced because at such a reference fluid pressure, a stronger interaction of the first mechanical oscillator with the reference fluid is present. Thus, e.g., a correction for a fluid-temperature- and fluid-pressure-dependence of the fluid viscosity is intrinsically taken care of (see below). However, for this, depending on the desired precision, also lower reference fluid pressures $p_R$ can be sufficient (hence the relatively wide variety of factors as discussed above) which reduces costs for more expensive reference fluids. It is also possible to establish a pressure balancing between the fluid and the reference fluid, e.g., through a flexible but fluid-impermeable membrane separating the measurement volume from the reference volume. Thus, fundamental errors during the derivation of $\rho_m$ or $\eta_m$ are reduced more efficiently.

In another advantageous embodiment, the method further comprises the step of deriving the fluid temperature $T_F$ by means of said first and/or said second mechanical oscillator(s). This can, e.g., be achieved by measuring a deviation of a difference between the resonance frequencies $f_R$ and $f_F$ from a difference between design frequencies $f_{d,R}$ and $f_{d,F}$ of said first and second mechanical oscillators while fluid and reference fluid densities are assumed to be constant (see below). Advantageously, thermal equilibrium between the fluid and the second mechanical oscillator is assumed as well as thermal equilibrium between the reference fluid and the first mechanical oscillator (if applicable). Thermal equilibrium between the fluid, the reference fluid, the first, and the second mechanical oscillator is even more advantageous. This can, e.g., be facilitated by utilizing materials with high thermal conductivities. Thus, the fluid temperature $T_F$ and the reference fluid temperature $T_R$ differ less and can be more easily derived.

Additionally or alternatively to deriving the fluid temperature $T_F$ by means of the mechanical oscillator(s), the fluid temperature $T_F$ and/or the reference fluid temperature $T_R$ (if applicable) are advantageously derived by means of at least one temperature sensor which is in direct or indirect contact with the respective fluid(s) and/or fluid comprising volume(s). Preferred temperature sensors comprise thermistors, resistance temperature detectors, thermocouples, integrated circuit (IC) temperature sensors, and/or optical temperature sensors. Thus, the fluid temperature $T_F$ and/or the reference fluid temperature $T_R$ (if applicable) can be more easily derived, e.g., also in multiple locations in the measurement volume and/or in the reference volume. Optional averaging of the single temperature readouts then also becomes possible, e.g., to address non-equilibrium states and to obtain a representative average temperature of the fluid.

In another advantageous embodiment, the method further comprises the step of deriving the fluid pressure $p_F$ and/or the reference fluid pressure $p_R$ (if applicable) by means of one or more pressure sensor(s) or by means of an equation relating temperatures with pressures. Such an equation can, e.g., be the ideal gas law, (i.e., $p_F V = n R T_F$ with V being a known volume value of the measurement volume, n being a number of gas molecules in the measurement volume (usually expressed in moles) and R being the universal gas constant). A similar equation applies for the reference volume. Thus, the derivation of the fluid pressure $p_F$ and/or the reference fluid pressure $p_R$ (if applicable) is simplified. Other equations relating the temperatures and the pressures can be used as well, e.g., the van-der-Waals equation, the virial equation, the Beattie-Bridgeman equation, or the Peng-Robinson equation. When an equation other than the ideal gas law is used, the behavior of a gas can be more accurately predicted than with the ideal gas law.

In another advantageous embodiment of the method, the fluid temperature $T_F$ and/or the reference fluid temperature $T_R$ (if applicable) and/or a temperature of said first mechanical oscillator and/or a temperature of said second mechanical oscillator is or are controlled by means of at least one temperature regulator. Such a temperature regulator can, e.g., comprise a (reference) fluid and/or oscillator heater, a (reference) fluid and/or oscillator cooler, and/or a feedback circuit operating the heater(s) and/or cooler(s). Thus, the temperature(s) can be actively influenced and, e.g., can be kept constant.

In another advantageous embodiment of the method, the first resonance frequency $f_R$ and the second resonance frequency $f_F$ are at least 1 kHz, preferably at least 30 kHz, more preferably at least 100 kHz. Thus, higher resonance frequencies can be used which helps to reduce fundamental errors during the derivation of $\rho_m$ or $\eta_m$ (see below).

More advantageously, a first design resonance frequency $f_{d,R}$ of said first mechanical oscillator is equal to or differs less than ±5%, preferably less than ±1% from a second design resonance frequency $f_{d,F}$ of said second mechanical oscillator. This has the advantage that the derivation of the estimated value $\rho_m$ or $\eta_m$ is facilitated. The term "design resonance frequency" in this respect relates to a resonance frequency of the respective mechanical oscillator which is determined during design and manufacturing of the mechanical oscillator. The measured first and second resonance frequencies $f_R$ and $f_F$ vary slightly from these design resonance frequencies due to interactions of the oscillator(s) with the fluid and the reference fluid (if applicable) and due to other influences such as temperature.

One equation that can advantageously be used to derive $\rho_m$ or $\eta_m$ indicative of $\rho$ or $\eta$ is $$|f_R - f_F| = |A\rho + \tilde{B}\sqrt{\rho}\sqrt{\eta} + C|$$

with A, B, and C being constants. In this equation, the desired variable $\rho$ or $\eta$ is then substituted by $\rho_m$ or $\eta_m$, respectively.

In an advantageous embodiment of the method, a fluid-temperature-dependent offset parameter $C(T_F)$ is used for deriving said estimated value $\rho_m$ or $\eta_m$. The fluid-temperature-dependent offset parameter $C(T_F)$ is indicative of a temperature-dependent frequency offset between said first and said second mechanical oscillators. This temperature-dependent frequency offset can be, e.g., due to mechanical differences between the two mechanical oscillators. The fluid-temperature-dependent offset parameter $C(T_F)$ can additionally or alternatively be indicative of a temperature-dependent frequency offset between a first oscillator circuit which is connected to said first mechanical oscillator and a second oscillator circuit which is connected to said second mechanical oscillator. The oscillator circuits are used to operate the respective mechanical oscillator (e.g. to induce resonant vibrations, to measure the respective resonance frequencies etc.). The temperature-dependence of the frequency offset can then be, e.g., due to a temperature dependence of the oscillator circuits itself, e.g., temperature-dependent capacitances or inductivities. By using a fluid-temperature-dependent offset parameter $C(T_F)$, temperature-dependent frequency offsets of the mechanical oscillators and/or their respective oscillator circuits can be more easily taken into account during the derivation of $\rho_m$ or $\eta_m$. A fluid-pressure-dependence of the offset parameter $C(T_F, p_F)$ can also be taken into account.

In another advantageous embodiment of the method, the estimated value $\eta_m$ which is indicative of the viscosity $\eta$ of the fluid is derived. This is, e.g., achieved by solving the equation $$|\eta_m(T_F)| = \left(\frac{|f_F - f_R| - (A\rho + C(T_F))}{\tilde{B}\sqrt{\rho}}\right)^2$$

with $f_R$ being said (reference fluid temperature-dependent) first resonance frequency, with $f_F$ being said (fluid temperature-dependent) second resonance frequency, with $\rho$ being a (known, pre-measured, or pre-modeled) density function of the fluid, with A and $\tilde{B}$ being oscillator-specific constants, and with $C(T_F)$ being a fluid-temperature-dependent frequency offset parameter between the first and second mechanical oscillators and/or oscillator circuits. Thus, the fluid temperature-dependent viscosity $\eta(T_F)$ of the fluid can be more easily estimated when the density $\rho$ is known. Fundamental errors during this estimation are avoided or reduced.

In another advantageous embodiment of the method, the estimated value $\rho_m$ which is indicative of the density $\rho$ of the fluid is derived. Thus, the density $\rho$ of the fluid which is an important parameter, e.g., in high-voltage switchgear, can be estimated and fundamental errors during this estimation are avoided or at least reduced.

In another advantageous embodiment, when the estimated value $\rho_m$ is derived, a reference-fluid-temperature-dependence $\delta\eta_R/\delta T_R$ of a viscosity function $\eta_R(T_R)$ of the reference fluid is equal to or differs less than ±30%, preferably less than ±10%, from a fluid-temperature-dependence $\delta\eta/\delta T_F$ of a viscosity function $\eta(T_F)$ of the fluid, at least for fluid temperatures $T_F$ and reference fluid temperatures $T_R$ in a range between 170 K and 400 K, preferably at least for fluid temperatures $T_F$ and reference fluid temperatures $T_R$ in a range between 220 K and 380 K. Thus, the temperature-dependences $\delta\eta/\delta T$ of the viscosity functions $\eta(T_F)$ and $\eta_R(T_R)$ of the fluid and the reference fluid (or, in other words, their slopes) are the same or at least similar. Thus, fundamental errors during the derivation of $\rho_m$ can be more easily avoided or reduced.

In another advantageous embodiment of the method, when the estimated value $\rho_m$ is derived, a (known, pre-measured, or pre-modeled) fluid-temperature-dependent viscosity function $\eta(T_F)$ is used during the derivation of the estimated value $\rho_m$. A plurality of values of $\eta$ for different fluid temperatures $T_F$ can, e.g., be pre-stored in a lookup-table or calculated on-the-fly, for example with fitting and/or inter- or extrapolation algorithms. Thus, fundamental errors during the derivation of $\rho_m$ can be more easily avoided or reduced.

In another advantageous embodiment of the method, when the estimated value $\rho_m$ is derived, a (known, pre-measured, or pre-modeled) fluid-pressure-dependent viscosity function $\eta(p_F)$ is used during the derivation of the estimated value $\rho_m$. A plurality of values of $\eta$ for different fluid pressures $p_F$ can, e.g., be prestored in a lookup-table or calculated on-the-fly, for example with fitting and/or inter- or extrapolation algorithms. Thus, fundamental errors during the derivation of $\rho_m$ can be more easily avoided or at least reduced.

In another advantageous embodiment of the method, the estimated value $\rho_m$ which is indicative of the density $\rho$ of the fluid is derived according to $$|f_R - f_F| = |A\rho_m + \tilde{B}\sqrt{\rho_m}\sqrt{\eta(p_F, T_F)} + C(p_F, T_F)|$$

with $$A = \frac{c_1 t}{2\rho_q w} f_d$$

and

-continued $$\tilde{B} = \frac{c_2}{2\rho_q w} \sqrt{\frac{f_d}{\pi}}$$

and with $c_1$, $c_2$, $t$, and $w$ being oscillator-geometry-dependent constants, with $\rho_q$ being an effective density of a material of said mechanical oscillators, with $\eta(p_F, T_F)$ being a fluid-pressure- and/or fluid-temperature-dependent viscosity function of said fluid, with $f_d$ being a common design resonance frequency of said first and said second mechanical oscillators (which is equal within ±5%, preferably within ±1% for both oscillators), and with $C(p_F, T_F)$ being a fluid-pressure- and/or fluid-temperature-dependent offset parameter which is indicative of a frequency offset between said first and said second mechanical oscillators and/or between a first oscillator circuit connected to and used to operate said first mechanical oscillator and a second oscillator circuit connected to and used to operated said second mechanical oscillator. The term "design resonance frequency" in this respect relates to a resonance frequency of the respective mechanical oscillator which is set during design and manufacturing of the mechanical oscillator. It should be noted that a temperature dependence $\delta C/\delta T$ and/or a pressure dependence $\delta C/\delta p$ of the offset parameter C can either be neglected, or it can advantageously be pre-measured or pre-modeled and used for calibration of the method, or—alternatively—the mechanical oscillators can be selected such that the temperature dependence $\delta C/\delta T$ is small, i.e., $\delta C/\delta T < 0.1$ Hz/K.

Here, the reference fluid temperature $T_R$ in Kelvin is equal to or differs less than ±5%, preferably less than ±2%, more preferably less than 1% from said fluid temperature $T_F$. Thermal equilibrium (equal temperatures) is more advantageously assumed for the fluid, the reference fluid, and the two mechanical oscillators.

Furthermore, a reference fluid pressure pR of the reference fluid is at most 0.1 mbar, preferably at most 10–2 mbar, more preferably at most 10–4 mbar over a reference fluid temperature range of TR>200 K and TR<400 K.

As an advantage, fundamental errors during the derivation of $\rho_m$ can be more easily avoided or reduced and the derivation of $\rho_m$ is simplified.

In a different advantageous embodiment of the method, the first mechanical oscillator is in contact with a reference fluid with a reference fluid pressure $p_R$ of at least 10 mbar, more preferably of at least 100 mbar, even more preferably of at least 1 bar over a reference fluid temperature range of $T_R$>200 K and $T_R$<400 K. Then, the estimated value $\rho_m$ which is indicative of the density $\rho$ of the fluid is derived according to $$|f_R - f_F| = \left| A_F \rho_m + \left( \tilde{B}_F \sqrt{\rho} - \tilde{B}_R \sqrt{\rho_R} \right) \cdot \sqrt{\eta(p_F, T_F)} + +D(p_F, T_F) \right|$$

with $$D(p_F, T_F) = C(p_F, T_F) - A_R \rho_R.$$

$A_F$, $A_R$, $\tilde{B}_F$, and $\tilde{B}_R$ are oscillator-geometry-dependent constants (with the index R for the first mechanical oscillator and with the index F for the second mechanical oscillator). $\rho_R$ is a (known) density of the reference fluid. The density $\rho$ of the fluid is equal to or differs less than ±50%, preferably less than ±10%, more preferably less than ±1% from the density $\rho_R$ of the reference fluid. $\eta(p_F, T_F)$ is a fluid-pressure- and/or fluid-temperature-dependent viscosity function of the fluid, which is equal to or differs less than ±50%, preferably less than ±10%, more preferably less than ±1% from a reference-fluid-pressure- and/or reference-fluid-temperature-dependent viscosity function $\eta_R(p_R, T_R)$ of the reference fluid. As above, $C(p_F, T_F)$ is a fluid-pressure- and/or fluid-temperature-dependent offset parameter which is indicative of a frequency offset between said first and said second mechanical oscillators and/or between a first oscillator circuit connected to and used to operate said first mechanical oscillator and a second oscillator circuit connected to and used to operated said second mechanical oscillator. The first and second mechanical oscillators (10, 20) are selected such that said oscillator-geometry-dependent constants $\tilde{B}_F$ and $\tilde{B}_R$ are equal to each other or differ less than ±50%, preferably less than ±10%, more preferably less than ±1%. Furthermore, the reference fluid temperature $T_R$ in Kelvin is equal to or differs less than ±5%, preferably less than ±2%, more preferably less than 1% from said fluid temperature $T_F$. Thermal equilibrium (equal temperatures) is more advantageously assumed for the fluid, the reference fluid, and the two mechanical oscillators.

As an advantage, fundamental errors during the derivation of $\rho_m$ can be more easily avoided or reduced and the derivation of $\rho_m$ is simplified.

In another advantageous embodiment of the method, said first mechanical oscillator, said second mechanical oscillator, said fluid, and said reference fluid have the same temperature, i.e., their temperatures do not differ by more than 1 K. As an advantage, this temperature can be used for deriving said estimated value $\rho_m$ and/or $\eta_m$.

As another aspect of the invention, a sensor for carrying out the method as described above is disclosed. The sensor comprises the first mechanical oscillator,
a first oscillator circuit connected to the first mechanical oscillator for operating (e.g., for inducing the resonant vibration, for measuring the first resonance frequency $f_R$ etc.) the first mechanical oscillator,
the second mechanical oscillator,
a second oscillator circuit connected to the second mechanical oscillator for operating (e.g., for inducing the resonant vibration, for measuring the second resonance frequency $f_R$ etc.) the second mechanical oscillator, and
an analysis and control unit connected to said first and second oscillator circuits and adapted to carry out the steps of said method.

Thus, a higher precision sensor that is less prone to fundamental errors, in particular due to fluid-temperature-dependent viscosities $\eta$, can be implemented.

Advantageously, the analysis and control unit of the sensor comprises a processing unit and a memory, wherein said analysis and control unit is adapted to derive at least two values of at least one fluid-temperature- and/or fluid-pressure-dependent parameter for at least two different fluid temperatures $T_F$ and/or for at least two different fluid pressures $p_R$. This can, e.g., be achieved by a lookup-table and/or by an on-the-fly calculation, e.g., including extra- or interpolation algorithms and fitting techniques. Thus, fluid-temperature- and/or fluid-pressure-dependent parameters can be more easily used for the derivation of $\rho_m$ or $\eta_m$.

In another advantageous embodiment, the sensor further comprises a sealed reference volume and a connector unit for connecting the sensor device to a fluid compartment (e.g., of a to-be-monitored apparatus) containing the to-bemeasured fluid. The first mechanical oscillator is arranged in said sealed reference volume which optionally comprises a reference fluid. Thus, the sensor can be manufactured, tested, and calibrated separately from the fluid-compartment.

As another aspect of the invention, a fluid-insulated electrical apparatus, in particular gas-insulated medium- or high-voltage switchgear, is disclosed. The fluid-insulated electrical apparatus comprises a sensor device as described above for deriving the estimated value $\rho_m$ indicative of the density $\rho$ of the to-be-quantified fluid and the to-be-quantified fluid in a fluid compartment of the electrical apparatus, wherein the fluid is adapted to insulate an electrically active part of the fluid-insulated electrical apparatus. Thus, a fluid-insulated electrical apparatus can be equipped with a higher precision density sensor.

Advantageously, the fluid of the fluid-insulated electrical apparatus comprises at least one of the components of the group consisting of nitrogen,
oxygen,
carbon dioxide,
nitric oxide,
nitrogen dioxide,
nitrous oxide,
argon,
methanes, in particular partially or fully halogenated methanes, in particular tetrafluoromethane or trifluoroiodomethane,
air, in particular technical air or synthetic air, and sulfur hexafluoride,
partially or fully fluorinated ethers, in particular hydrofluoroethers, hydrofluoro monoethers, hydrofluoro monoethers containing at least 3 carbon atoms, perfluoro monoethers, or perfluoro monoethers containing at least 4 carbon atoms,
partially or fully fluorinated ketones, in particular hydrofluoro monoketones, perfluoro monoketones, perfluoro monoketones comprising at least 5 carbon atoms, or perfluoro monoketones comprising exactly 5 or 6 or 7 or 8 carbon atoms, and
mixtures thereof.

Thus, a higher insulation strength can be achieved.

As another aspect of the invention, a computer program element comprising computer program code means for, when executed by a processing unit, implementing a method as described above is disclosed. This enables the implementation of a method as described above into a device comprising a processing unit.

BRIEF DESCRIPTION OF THE DRAWINGS

The invention and its embodiments will be more fully appreciated by reference to the following detailed description of advantageous but nonetheless illustrative embodiments in accordance with the present invention when taken in conjunction with the accompanying drawings.

BRIEF DESCRIPTION OF THE INVENTION

Description of the Figures

Figure 1:
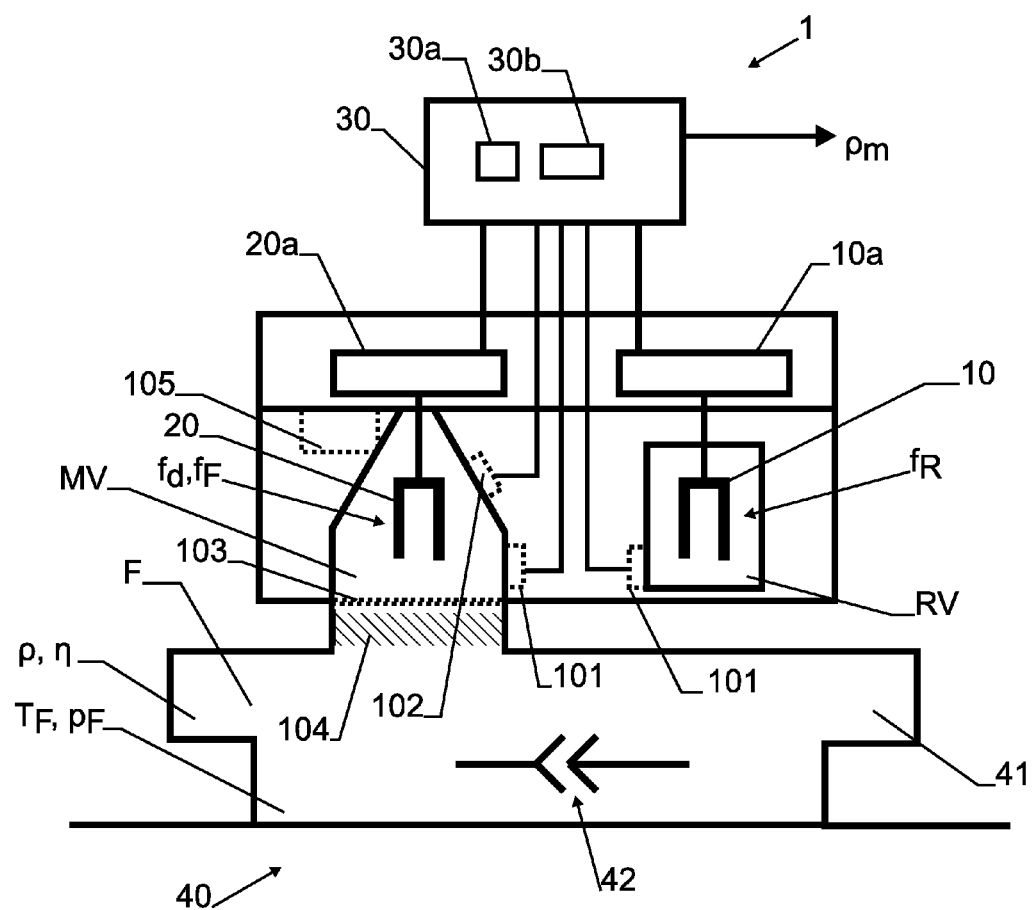
FIG. 1 shows a fluid-insulated electrical apparatus 40 with a sensor 1 according to a first embodiment of the invention, wherein a fluid-temperature-dependent viscosity $\eta(T_F)$ is used for deriving an estimated value $\rho_m$.

FIG. 1 shows a fluid-insulated electrical apparatus 40 with a sensor 1 according to a first embodiment of the invention. A fluid-temperature-dependent viscosity function $\eta(T_F)$ is used in this embodiment for deriving an estimated value $\rho_m$ which is indicative of a density $\rho$ of a fluid F (see below). The electrical apparatus 40 comprises a fluid compartment 41 which comprises an insulation fluid F (e.g. an insulation gas comprising $SF_6$) for insulating an electrically active part 42 of the electrical apparatus 40. The insulation fluid has a fluid pressure $p_F$=3.5 bar, a fluid temperature $T_F$=20° C., a viscosity $\eta$=14 µPa s and a density $\rho$=4.09 kg/m³. A gas permeable protective mesh 104 can be arranged near a flange on the fluid compartment 41 for preventing the passage of particles and undesired chemical compounds which could damage a connected sensor 1. A connector unit 103 of a sensor 1 connects a measurement volume MV of the sensor 1 to the fluid compartment 41 of the electrical apparatus 40. In the measurement volume MV, a second mechanical oscillator (quartz tuning fork, e.g. model CFS206 from Citizen) with a design resonance frequency of $f_d$=32.768 k Hz is arranged. This tuning fork is in contact with the fluid F. An oscillator circuit 20a induces a resonant vibration in the tuning fork, but due to interactions with the fluid F, the second resonance frequency $f_F$=32.758 kHz slightly varies from the design resonance frequency $f_d$. Furthermore, the second resonance frequency $f_F$ is temperature dependent due to fork-material and oscillator circuit properties. The second mechanical oscillator as well as the second oscillator circuit 20a are in thermal equilibrium with the fluid F, i.e., they have the same temperature $T_F$. This can, e.g., be facilitated by an optional temperature regulator 105 (dotted) and/or a sensor housing with a high thermal conductivity. Optional temperature sensors 101 (dotted) and/or an optional pressure sensor 102 (dotted) can be used to measure the temperature $T_F$ and/or the pressure $p_F$ of the fluid F as well as a temperature of the first mechanical oscillator. As an alternative to using a temperature sensor 101, the deviation of the second resonance frequency $f_F$ from the design resonance frequency $f_d$ can be used to quantify the fluid temperature $T_F$, when a constant fluid density $\rho$ in the measurement volume MV is assumed.

In a sealed reference volume RV of the sensor 1, a first mechanical oscillator 10 is arranged (pressure $p_R$ at most $10^{-4}$ mbar). The first mechanical oscillator is also a quartz tuning fork e.g. of the same type and the same design resonance frequency $f_d$ as the second mechanical oscillator 20. An oscillator circuit 10a induces a resonant vibration in the first mechanical oscillator 10, but due to the missing interactions with the fluid F, the first resonance frequency $f_R$=32.768 kHz slightly varies from the second resonance frequency $f_F$ of the second mechanical oscillator 20. The first resonance frequency $f_R$ can also slightly vary from the design resonance frequency $f_d$ due to temperature dependencies of the first mechanical oscillator 10 and the oscillator circuit 10a. In other words, also the first resonance frequency $f_R$ is temperature dependent. The first mechanical oscillator 10 is not in contact with the fluid F, but in thermal equilibrium with the fluid F and the second mechanical oscillator 20. Therefore, also the deviation of the difference between the resonance frequencies $f_R$ and $f_F$ from the difference of the design frequencies $f_{d,R}$ and $f_{d,F}$ can be used to quantify the fluid temperature $T_F$, while fluid and reference fluid densities are assumed to be constant.

The values of $f_F$ and $f_R$ are read out by the oscillator circuits 10a and 20a and transmitted to an analysis and control unit 30 comprising a processing unit 30a and a memory 30b.

Using these resonance frequencies $f_R$ and $f_F$, the processing unit 30 derives an estimated value $\rho_m$ which is indicative of the density $\rho$ of the fluid F according to $$|f_R - f_F| = |A\rho_m + \tilde{B}\sqrt{\rho_m}\sqrt{\eta(T_F)} + C(T_F)| \quad \text{eq. 1}$$

with $$A = \frac{c_1 t}{2\rho_q w} f_d$$

and $$\tilde{B} = \frac{c_2}{2\rho_q w}\sqrt{\frac{f_d}{\pi}}$$

and with $c_1$, $c_2$, t, and w being tuning-fork-geometry-dependent constants. $\rho_q$ is an effective density of the material of the second mechanical oscillator 20. $f_d$ is the design resonance frequency of the second mechanical oscillator 20.

In this embodiment, a fluid-temperature-dependent viscosity function $\eta(T_F)$ (see FIG. 2) of the fluid F is used for deriving the estimated value $\rho_m$. Alternatively, also a viscosity function $\eta(p_F, T_F)$ taking into account the fluid pressure $p_F$ could be used (not shown here). This function is pre-stored in the memory 30b as a lookup table for different fluid temperature values $T_F$. Interpolation algorithms can furthermore be used. The parameter $C(T_F)$ is a fluid-temperature-dependent frequency offset parameter which is indicative of a manufacturing tolerance-induced frequency offset between said first and said second mechanical oscillators 10 and 20 and their respective oscillator circuits 10a and 20a. This parameter also describes fluid-temperature-dependences $\delta f/\delta T$ of the first and second resonance frequencies $f_R$ and $f_F$ and it is also pre-stored in the memory 30b for different temperatures T. A parameter $C(p_R, T_R)$ that is also pressure-dependent is also possible (not shown here).

Figure 3:
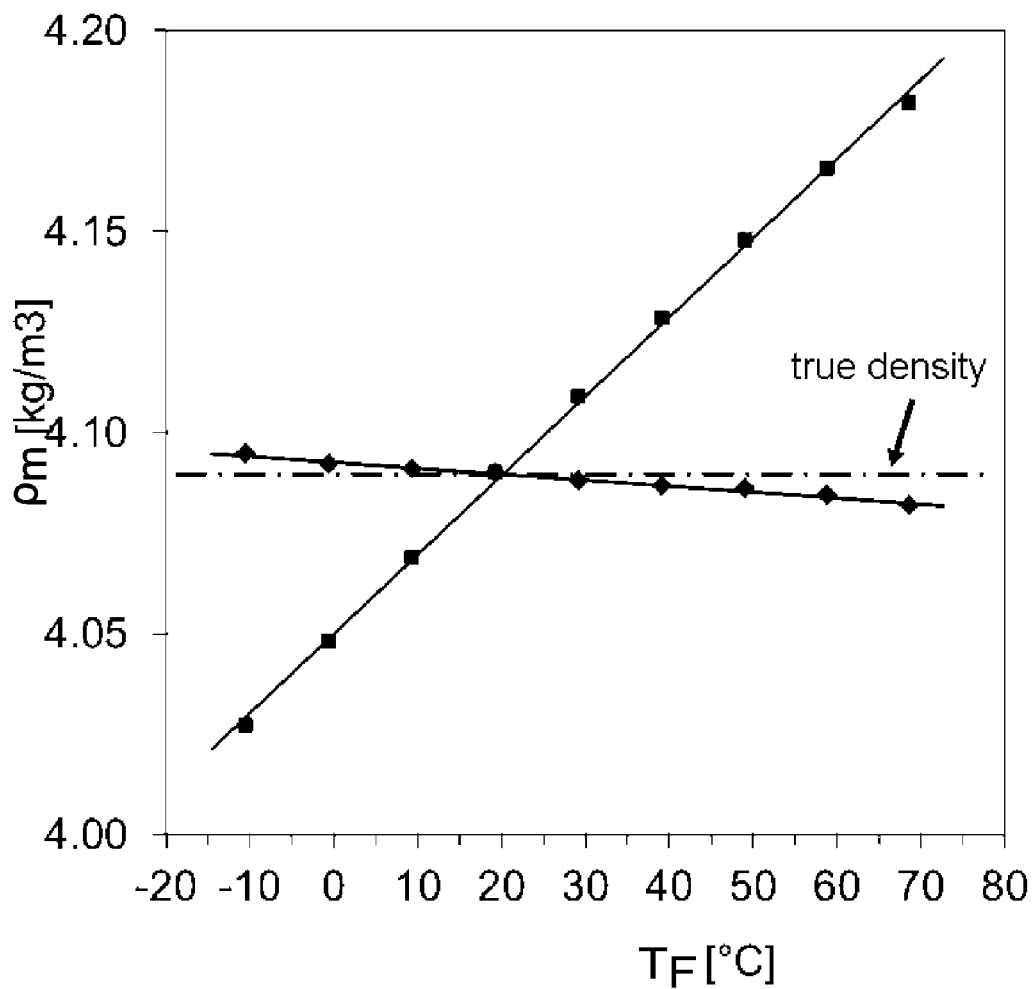
FIG. 3 shows a dependence of an estimated value $\rho_m$ of a fluid temperature $T_F$, wherein $\rho_m$ is derived with different methods for comparison.

By using a fluid-temperature-dependent viscosity function $\eta(T_F)$ and a fluid-temperature-dependent frequency offset parameter $C(T_F)$, fundamental errors in the derivation of the estimated values $\rho_m$ (or alternatively $\eta_m$ in a similar embodiment) can be avoided or reduced (see FIG. 3). As stated above, also a pressure dependency of $\eta(p_F)$ and $C(p_F)$ can be taken into account. The effect of such corrections is an order of magnitude smaller than the temperature dependence, however. Specifically, the change of viscosity $\eta$ with pressure is approximately $\delta\eta/\delta p = 0.5\%10$ bar in the range between 0.1 bar and 10 bar, while the change of viscosity $\eta$ with temperature is approximately $\delta\eta/\delta T = 5\%100$ K in the range between 100 K and 400 K.

It should be noted that resonance frequencies $f_R$ and $f_F$ of at least 1 kHz, preferably at least 30 kHz, more preferably at least 100 kHz of the mechanical oscillators also lead to reduced fundamental viscosity-induced errors in the derivation of $\rho_m$, because $\tilde{B}\sqrt{\eta(T_F)} \propto \sqrt{f_d}\sqrt{\eta(T_F)}$ while $A \propto f$ and thus the contribution of the viscosity-dependent term becomes smaller with increasing resonance frequencies $f_R$ and $f_F$. Zeisel et al., "A precise and robust quartz sensor based on tuning fork technology for ($SF_6$)-gas density control", Sensors and Actuators 80 (2000), 233-236 give more details on this.

Figure 2:
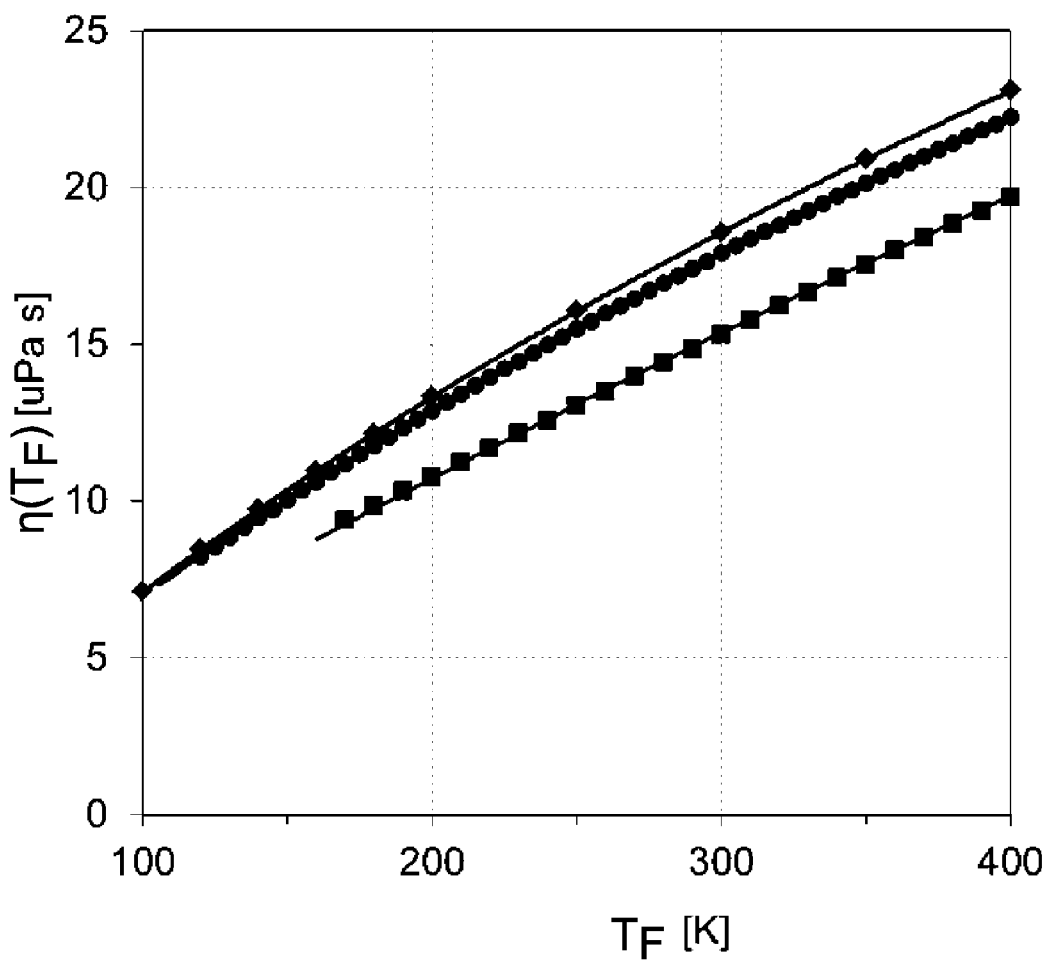
FIG. 2 shows a viscosity function $\eta(T_F)$ as a function of a fluid temperature $T_F$ for different gases.

FIG. 2 shows a viscosity function $\eta(T_F)$ as a function of a fluid temperature $T_F$ for different gases. Such a viscosity function $\eta(T_F)$ is used in the first embodiment of the invention as described with regard to FIG. 1. Specifically here, diamonds show a viscosity $\eta$ for dry air at a pressure of 1 bar, circles show a viscosity $\eta$ for nitrogen at a pressure of 1 bar, and rectangles show a viscosity $\eta$ for $SF_6$. All gases show a similar temperature dependence $\delta\eta/\delta T$. Lines are $3^{rd}$ order polynomial fits through the measured points. By using a fluid-temperature-dependent viscosity function $\eta(T_F)$, fundamental errors in the derivation of the estimated values $\rho_m$ (or $\eta_m$) can be avoided or reduced.

FIG. 3 shows an estimated value $\rho_m$ as a function of a fluid temperature $T_F$ as obtained from the first embodiment of the invention as described with regard to FIG. 1. Furthermore, different correction approaches are compared. Specifically, rectangles show prior-art estimated values $\rho_m$ as obtained with a constant (i.e., non-fluid-temperature-dependent) viscosity $\eta$. As it can be seen, a mis-estimation of the density $\rho$ of the fluid F of ±2% results in a temperature range between −10° C. and +70° C. with such an approach due to a fundamental temperature error neglecting the fluid-temperature-dependence of the viscosity $\eta$.

In contrast, diamonds show estimated values $\rho_m$ as obtained when taking into account a fluid-temperature dependent viscosity function $\eta(T_F)$ as shown in FIG. 2, i.e. according to the present application. Obviously, these estimations are much closer to a true density value $\rho$, the mis-estimation of the density $\rho$ being reduced to ±0.1% over the same temperature range. The true density $\rho$ is shown with a dashed-dotted line. All other lines are linear fits.

Figure 4:
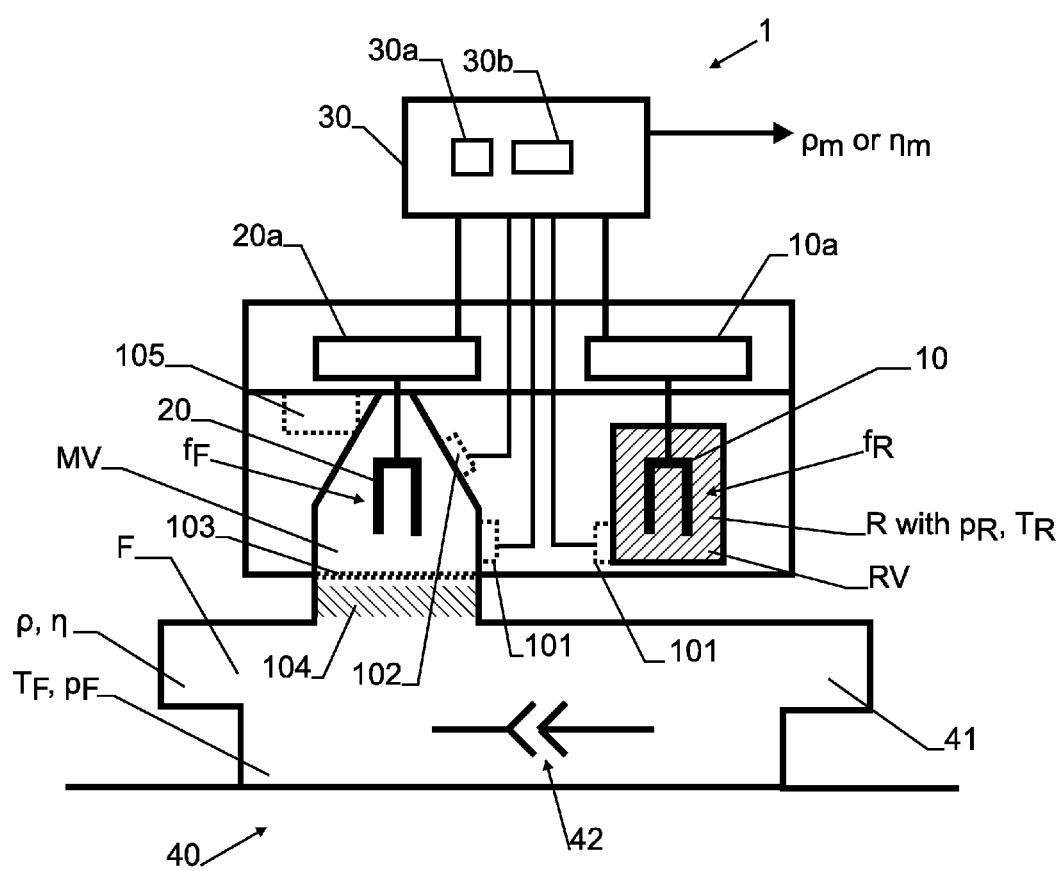
FIG. 4 shows a fluid-insulated electrical apparatus 40 with a sensor 1 according to a second embodiment of the invention, wherein a reference volume RV comprises a reference fluid R which is in contact with a first mechanical oscillator 10.

FIG. 4 shows a fluid-insulated electrical apparatus 40 with a sensor 1 according to a second embodiment of the invention. The second embodiment is very similar to the first embodiment described with regard to FIG. 1. Therefore, the same reference symbols are used. One difference between the first embodiment and the second embodiment is that the reference volume RV in the second embodiment comprises a reference fluid R with a reference fluid pressure $p_R$ and a reference fluid temperature $T_R$. The reference fluid R is in contact with the first mechanical oscillator 10. Being exposed to the reference fluid R, which is the same or a similar fluid (see above, i.e. similar in terms of densities $\rho$ and $\rho_R$, similar in terms of viscosity functions $\eta(p_F, T_F)$ and $\eta_R(p_R, T_R)$ and their temperature-dependences $\delta\eta/\delta T$), the first (reference) mechanical oscillator will also respond to the same effects like the second (fluid-embedded) mechanical oscillator, provided that the fluid and the reference fluid have the same or at least similar (see above) temperatures $T_F$ and $T_R$. This can, e.g., be facilitated by an optional temperature regulator 105 (dotted) and/or a sensor housing with a high thermal conductivity. In this second embodiment, the reference fluid pressure $p_R$ is 1 bar. Thus, pressure-dependent effects on the viscosity are similar for the fluid F and the reference fluid R. Fluid temperature $T_F$ and reference fluid temperature $T_R$ can be measured by temperature sensors 101. In this embodiment, the following equation is used for deriving the estimated value $\rho_m$ $$|f_R - f_F| = \left| A_F \rho_m + (\tilde{B}_F \sqrt{\rho} - \tilde{B}_R \sqrt{\rho_R}) \cdot \sqrt{\eta(p_F, T_F)} + + D(p_F, T_F) \right|$$

with the same definitions as discussed above.

By arranging the first mechanical oscillator 10 in contact with a reference fluid, fundamental errors in the derivation of the estimated values $\rho_m$ or $\eta_m$ can be intrinsically avoided or reduced.

Definitions:

The term "fluid" relates to "a substance, such as a liquid [and/] or gas, that can flow, has no fixed shape, and offers little resistance to an external stress" (from http://www.thefreedictionary.com/fluid, accessed on Sep. 11, 2011).

The term "high-voltage" relates to voltages larger than 50 kV.

The term "medium-voltage" relates to voltages larger than 1 kV.

Note:

While there are shown and described presently preferred embodiments of the invention, it is to be distinctly understood that the invention is not limited thereto but may be otherwise variously embodied and practiced within the scope of the following claims.

REFERENCE SYMBOLS 1 sensor
10 first mechanical oscillator
101 temperature sensor
102 pressure sensor
103 connector unit
104 protective mesh
105 temperature regulator
10a first oscillator circuit
20 second mechanical oscillator
20a second oscillator circuit
30 analysis and control unit
30a processing unit
30b memory
40 fluid-insulated electrical apparatus
41 fluid compartment
42 electrically active part
$C(T_F, p_F)$ frequency offset parameter
F fluid
$f_d$ design resonance frequency
$f_R$ first resonance frequency
$f_F$ second resonance frequency
MV measurement volume
p pressure
$p_F$ fluid pressure
$p_R$ reference fluid pressure
R reference fluid
RV reference volume
T temperature
$T_F$ fluid temperature
$T_R$ reference fluid temperature
$\eta(T_F, p_F)$ viscosity function of fluid
$\eta_m$ estimated value indicative of viscosity h of fluid
$\rho_m$ estimated value indicative of density $\rho$ of fluid
$\delta\eta/\delta T_R$ reference-fluid-temperature-dependence of a viscosity function $\eta(T_R)$
$\delta\eta/\delta T_F$ fluid-temperature-dependence of a viscosity function $\eta(T_F)$
$\delta f_R/\delta T_R$ reference-fluid-temperature-dependence of a first resonance frequency $f_R$
$\delta f_F/\delta T_F$ fluid-temperature-dependence of a second resonance frequency $f_F$
$\delta C/\delta T$ temperature dependence of C
$\delta C/\delta p$ pressure dependence of C
$\eta_R(p_R, T_R)$ reference-fluid-pressure- and/or reference-fluid-temperature-dependent viscosity function of the reference fluid
$\rho_R$ density of reference fluid

The invention claimed is:

1. A method for deriving an estimated value $\rho_m$ which is indicative of a density $\rho$ of a fluid with a fluid temperature $T_F$ and a fluid pressure $p_F$, the method comprising the steps of:
   a) measuring a first resonance frequency $f_R$ of a resonant vibration of a first mechanical oscillator, wherein said first mechanical oscillator is arranged in a reference volume and wherein said first mechanical oscillator is secluded from said fluid;
   b) measuring a second resonance frequency $f_F$ of a resonant vibration of a second mechanical oscillator, wherein said second mechanical oscillator is arranged in a measurement volume, wherein said measurement volume comprises said fluid, and wherein said fluid is in contact with said second mechanical oscillator;
   c) deriving said estimated value $\rho_m$ using said first resonance frequency $f_R$ and said second resonance frequency $f_F$;
   wherein in said step c) said fluid temperature $T_F$ and/or said fluid pressure $p_F$ and/or at least one parameter which is dependent on said fluid temperature $T_F$ and/or on said fluid pressure $p_F$ is/are used for deriving said estimated value $\rho_m$;
   wherein in said step c) a fluid-temperature-dependent viscosity function $\eta(T_F)$ is used for deriving said estimated value $\rho_m$, wherein the fluid-temperature-dependent viscosity function $\eta(T_F)$ is known, pre-measured or pre-modeled;
   wherein said estimated value $\rho_m$, which is indicative of said density $\rho$ of said fluid, is derived; and
   wherein in said step c) a fluid-temperature-dependent offset parameter $C(T_F)$ is used for deriving said estimated value $\rho_m$, wherein said fluid-temperature-dependent offset parameter $C(T_F)$ is indicative of a temperature-dependent frequency offset between said first and said second mechanical oscillators, and/or between a first oscillator circuit connected to and used to operate said first mechanical oscillator and a second oscillator circuit connected to and used to operate said second mechanical oscillator.

2. The method of claim 1, wherein a plurality of values of $\eta$ for different fluid temperatures $T_F$ are pre-stored in a lookup-table or calculated on-the-fly.

3. The method of claim 1, wherein in said step c) a fluid-pressure-dependent viscosity function $\eta(p_F)$ is used for deriving said estimated value $\rho_m$, wherein a plurality of values of $\eta$ for different fluid pressures $p_F$ are prestored in a lookup-table or calculated on-the-fly, by fitting and/or interpolation or extrapolation algorithms.

4. The method of claim 1,
   wherein in said step c) a fluid-pressure-dependence of the offset parameter $C(T_F, p_F)$ is also used for deriving said estimated value $\rho_m$.

5. The method of claim 1, wherein a reference-fluid-temperature-dependence $\delta\eta/\delta T_F$ of a viscosity function $\eta(T_R)$ of the reference fluid is equal to or differs less than ±30% from a fluid-temperature-dependence $\delta\eta/\delta T_F$ of the fluid-temperature-dependent viscosity function $\eta(T_F)$ of said fluid, at least for fluid temperatures $T_F$ and reference fluid temperatures $T_R$ in a range between 170 K and 400 K.

6. The method of claim 1, wherein said estimated value $\rho_m$ is derived according to:

$$|f_R - f_F| = \left| A\rho_m + \tilde{B}\sqrt{\rho_m}\sqrt{\eta(p_f, T_f)} + C(p_F, T_F) \right|$$

with $$A = \frac{c_1 t}{2\rho_q w} f_d$$

and $$\tilde{B} = \frac{c_2}{2\rho_q w}\sqrt{\frac{f_d}{\pi}}$$

and with $c_1$, $c_2$, $t$, and $w$ being oscillator-geometry-dependent constants, with $\rho_q$ being an effective density of a material of said mechanical oscillators with $\eta(p_F, T_F)$ being a fluid-pressure- and/or fluid-temperature-dependent viscosity function of said fluid, with $f_d$ being a common design resonance frequency of said first and second mechanical oscillators, and with $C(p_F, T_F)$ being a fluid-pressure- and/or fluid-temperature-dependent offset parameter which is indicative of a frequency offset between said first and said second mechanical oscillator and/or between a first oscillator circuit connected to said first mechanical oscillator and a second oscillator circuit connected to said second mechanical oscillator;

wherein said reference fluid temperature $T_R$ in Kelvin is equal to or differs less than ±5%, from said fluid temperature $T_F$; and wherein a reference fluid pressure $p_R$ of a reference fluid is at most 0.1 mbar over a reference fluid temperature range of $T_R$>200 K and $T_R$<400 K.

7. The method of claim 1, wherein said first mechanical oscillator is in contact with a reference fluid with a reference fluid pressure $p_R$ of at least 10 mbar, over a reference fluid temperature range of $T_R$>200 K and $T_R$<400 K; and wherein said estimated value $\rho_m$ is derived according to $$|f_R - f_F| = \left| A_F\rho_m + (\tilde{B}_F\sqrt{\rho} - \tilde{B}_R\sqrt{\rho_R})\cdot\sqrt{\eta(p_F, T_F)} ++D(p_F, T_F) \right|$$

with $$D(p_F, T_F) = C(p_F, T_F) - A_R\rho_R$$

with $A_F$, $A_R$, $\tilde{B}_F$, and $\tilde{B}_R$ being oscillator-geometry-dependent constants, with subscripts R, F relating to the first and second mechanical oscillator, respectively;

with $\rho_R$ being a density of said reference fluid, wherein said density $\rho$ of said fluid is equal to or differs less than ±50% from said density $\rho_R$ of said reference fluid;

with $\eta(p_F, T_F)$ being a fluid-pressure- and/or fluid-temperature-dependent viscosity function of said fluid, which is equal to or differs less than ±50% from a reference-fluid-pressure- and/or reference-fluid-temperature-dependent viscosity function $\eta_R(p_R, T_R)$ of said reference fluid;

and with $C(p_F, T_F)$ being a fluid-pressure- and/or fluid-temperature-dependent offset parameter which is indicative of a frequency offset between said first and said second mechanical oscillators and/or between a first oscillator circuit connected to said first mechanical oscillator and a second oscillator circuit connected to said second mechanical oscillator;

wherein said first and second mechanical oscillators are selected such that said oscillator-geometry-dependent constants $\tilde{B}_F$ and $\tilde{B}_R$ are equal or differ less than ±50% from each other; and wherein said reference fluid temperature $T_R$ in Kelvin is equal to or differs less than ±5% from said fluid temperature $T_F$.

8. The method of claim 1, wherein said fluid temperature $T_F$ and/or a reference fluid temperature $T_R$ and/or a temperature of said first mechanical oscillator and/or a temperature of said second mechanical oscillator is or are controlled by at least one temperature regulator.

9. The method of claim 1, wherein said first mechanical oscillator, said second mechanical oscillator, said fluid, and said reference fluid have the same temperature.

10. The method of claim 1, wherein said first mechanical oscillator is in contact with a reference fluid with a reference fluid temperature $T_R$ and a reference fluid pressure $p_R$, and said reference volume comprises said reference fluid.

11. The method of claim 1, wherein the temperature dependence $\delta C/\delta T$ of the offset parameter C is pre-measured or pre-modeled and is used for calibration of the method, or that the mechanical oscillators are selected such that the temperature dependence $\delta C/\delta T$ is less than 0.1 Hz/K.

12. The method of claim 1, further comprising deriving an estimated value $\eta_m$ indicative of a viscosity $\eta$ of the fluid, using said first resonance frequency $f_R$ and said second resonance frequency $f_F$;

wherein said fluid temperature $T_F$ and/or said fluid pressure $p_F$ and/or at least one parameter which is dependent on said fluid temperature $T_F$ and/or on said fluid pressure $p_F$ is/are used for deriving said estimated value $\eta_m$; and wherein said first mechanical oscillator is in contact with a reference fluid with a reference fluid temperature $T_R$ and a reference fluid pressure $p_R$, said reference volume comprises said reference fluid, and said reference fluid temperature $T_R$ in Kelvin is equal to or differs less than ±5% from said fluid temperature $T_F$.

13. The method of claim 12, wherein said reference fluid pressure $p_R$ is at most 0.1 mbar over a reference fluid temperature range of $T_R$>200 K and $T_R$<400 K, or said reference fluid pressure $p_R$ is at least 1 mbar over a reference fluid temperature range of $T_R$>200 K and $T_R$<400 K.

14. The method of claim 12, further comprising the step of deriving said fluid temperature $T_F$ by said first and/or said second mechanical oscillator; and/or deriving said fluid temperature $T_F$ and/or a reference fluid temperature $T_R$ by at least one temperature sensor, a resistance temperature detector, a thermocouple, an integrated circuit temperature sensor, and/or an optical temperature sensor.

15. The method of claim 12, wherein the estimated value $\eta_m$ which is indicative of the viscosity n of the fluid is derived by solving the equation $$|\eta_m(T_F)| = \left(\frac{|f_F - f_R| - (A\rho + C(T_F))}{\tilde{B}\sqrt{\rho}}\right)^2$$

with $f_R$ being said reference fluid temperature-dependent first resonance frequency, with $f_F$ being said fluid temperature-dependent second resonance frequency, with ρ being a known, pre-measured, or pre-modeled density function of the fluid, with A and $\hat{B}$ being oscillator-specific constants, and with $C(T_F)$ being a fluid-temperature-dependent frequency offset parameter between the first and second mechanical oscillators and/or oscillator circuits.

* * * * *